(12) United States Patent
Kerr

(10) Patent No.: US 11,026,985 B2
(45) Date of Patent: Jun. 8, 2021

(54) METHODS FOR REMOVING CONTAMINANTS FROM PLANT-DERIVED PHARMACEUTICALS

(71) Applicant: Sorbent Technologies, Inc., Norcross, GA (US)

(72) Inventor: Robert Ralph Kerr, Alpharetta, GA (US)

(73) Assignee: Sorbent Technologies, Inc., Norcross, GA (US)

( * ) Notice: Subject to any disclaimer, the term of this patent is extended or adjusted under 35 U.S.C. 154(b) by 0 days.

(21) Appl. No.: 16/572,678

(22) Filed: Sep. 17, 2019

(65) Prior Publication Data

US 2020/0093876 A1    Mar. 26, 2020

Related U.S. Application Data

(60) Provisional application No. 62/732,481, filed on Sep. 17, 2018.

(51) Int. Cl.
| | | |
|---|---|---|
| *A61K 36/00* | (2006.01) | |
| *A61K 36/185* | (2006.01) | |
| *B01J 20/10* | (2006.01) | |
| *B01J 20/28* | (2006.01) | |

(52) U.S. Cl.
CPC ........... *A61K 36/185* (2013.01); *B01J 20/103* (2013.01); *B01J 20/28047* (2013.01); *A61K 2236/33* (2013.01); *A61K 2236/53* (2013.01); *B01J 2220/603* (2013.01); *B01J 2220/80* (2013.01)

(58) Field of Classification Search
None
See application file for complete search history.

(56) References Cited

U.S. PATENT DOCUMENTS 9,956,498 B1    5/2018    Tucker

FOREIGN PATENT DOCUMENTS

| CN | 103524521 A | * | 1/2014 |
|---|---|---|---|
| CN | 105061554 A | * | 11/2015 |
| CN | 103698463 B | | 12/2015 |
| CN | 106009566 A | * | 10/2016 |
| CN | 107593896 A | * | 1/2018 |
| IN | 9601355 I2 | * | 9/2016 |
| WO | 2003/064407 A2 | | 8/2003 |

OTHER PUBLICATIONS

PCT/US2019/051378 International Search Report and Written Opinion, dated Nov. 28, 2019.

* cited by examiner

*Primary Examiner* — Qiuwen Mi
(74) *Attorney, Agent, or Firm* — Withers & Keys, LLC

(57) ABSTRACT

Methods of removing contaminants such as pesticides, herbicides, and fungicides from plant-derived pharmaceuticals, such as *Cannabis*-derived pharmaceuticals, are disclosed. Plant-derived pharmaceuticals, such as *Cannabis*-derived pharmaceuticals, and methods of using the plant-derived pharmaceuticals are also disclosed.

20 Claims, 2 Drawing Sheets

METHODS FOR REMOVING CONTAMINANTS FROM PLANT-DERIVED PHARMACEUTICALS

CROSS-REFERENCE TO RELATED APPLICATIONS

This patent application claims the benefit of priority to U.S. Provisional Patent Application Ser. No. 62/732,481 filed on Sep. 17, 2018 and entitled "METHODS FOR REMOVING CONTAMINANTS FROM PLANT-DERIVED PHARMACEUTICALS," the subject matter of which is hereby incorporated by reference in its entirety.

FIELD OF THE INVENTION

The present invention relates generally to methods of removing contaminants such as pesticides, herbicides and fungicides from plant-derived pharmaceuticals such as *Cannabis*-derived pharmaceuticals. The present invention further relates to plant-derived pharmaceuticals and methods of using the plant-derived pharmaceuticals.

BACKGROUND OF THE INVENTION

The plant genus *Cannabis* is cultivated for a variety of reasons, one of which is to obtain the organic substances made by the plant called Cannabinoids that are unique to the genus.

Pesticides, synergists, herbicides, and fungicides collectively referred to herein as "contaminants," are used by cultivators to increase crop yield and crop quality. Some of the contaminants are applied directly to the plants. Some contaminants pollute the crop after application to crops in adjacent fields. Some contaminants are persistent and remain in the soil from previous crops.

Cannabinoids are extracted from the plant matrix by a variety of methods, the most prominent of which are: solvent extraction and supercritical fluid extraction. In any case, the cannabinoids are extracted and concentrated from the plant matrix with a resulting oily, semi-solid material.

The extraction processes for removing and concentrating cannabinoids also remove and concentrate the toxic contaminants. All solvents extract a relatively broad range of substances. Further, substances with similar characteristics are always extracted together. In terms of solubility in common solvents, the cannabinoids and the contaminants have very similar properties, and consequently, are typically extracted together.

Health authorities in some states have set permissible limits on the concentration of individual contaminants in *Cannabis*. In the Oregon Health Authorities Technical Report 8964, some 59 contaminants, primarily pesticides, synergists, and fungicides, must be tested in *Cannabis* and *Cannabis*-containing products before they can be sold.

Testing for contaminants in *Cannabis* products has commenced in several states in the United States. It has been found that the extracts contain relatively elevated amounts of contaminants that are a danger to human health.

In general, the methods available to obtain *Cannabis* extracts with safe levels of contaminants are: (1) pesticide-free crop growth, (2) selective extraction, (3) selective adsorption, and (4) chromatographic purification. It is also possible to destroy contaminants by selective chemical reaction; however, this method is not typically employed since there are very few situations in which the desired components differ significantly in their chemical reactivity towards specific reactant relative to the contaminants.

Generally speaking, dried material of *Cannabis sativa* contains about 10% cannabinoids and *Cannabis indica* (or hemp) contains 3-5% cannabinoids. Even when the raw plant materials are measured to have low or acceptable levels of contaminants, after known extraction and concentration techniques, the *Cannabis* extracts show a significant increase in contaminant concentration using the conventional techniques discussed above. Generally, the contaminant concentration is typically increased by a factor of 10-fold using the conventional techniques discussed above.

There is a need for simple, effective, safe, and environmentally-friendly methods of removing contaminants from plant-derived pharmaceuticals such as *Cannabis*-derived extracts.

SUMMARY OF THE INVENTION

The present invention is directed to simple, effective, safe, and environmentally-friendly methods of removing contaminants from plant-derived pharmaceuticals. The disclosed methods efficiently and safely enable proper removal of contaminants such as pesticides, herbicides, fungicides, etc. from plant-derived pharmaceuticals. The disclosed methods also provide a cost-effective and convenient method of removing contaminants from plant-derived pharmaceuticals.

In some embodiments of the present invention, the method of removing contaminants from plant-derived pharmaceuticals comprises: reacting one or more contaminants within a plant-derived extract with an alkali metal hydroxide in a polar solvent (e.g., an alcohol) to form one or more contaminant by-products; and separating the one or more contaminant by-products from the plant-derived extract so as to obtain a contaminant-reduced, plant-derived extract.

The present invention is further directed to contaminant-reduced, plant-derived extracts formed using the herein-disclosed methods of removing contaminants from plant-derived pharmaceuticals. In some embodiments of the present invention, the contaminant-reduced, plant-derived extracts formed using the herein-disclosed methods of removing contaminants from plant-derived pharmaceuticals comprise cannabinoids.

The present invention is even further directed to methods of using contaminant-reduced, plant-derived extracts to treat a patient suffering from one or more diseases or disorders. In some embodiments of the present invention, the method of using contaminant-reduced, plant-derived extracts comprises administering an effective amount of the contaminant-reduced, plant-derived extract to the patient, and the contaminant-reduced, plant-derived extract comprises one or more cannabinoids.

These and other features and advantages of the present invention will become apparent after a review of the following detailed description of the disclosed embodiments and the appended claims.

BRIEF DESCRIPTION OF THE FIGURES

The present invention is further described with reference to the appended figure, wherein.

DETAILED DESCRIPTION OF THE INVENTION

The present invention is directed towards methods of removing contaminants from plant-derived pharmaceuticals. The present invention is further directed towards plant-derived pharmaceuticals obtained using the herein-described methods, and methods of using the plant-derived pharmaceuticals.

I. Methods of Removing Contaminants from Plant-Derived Pharmaceuticals

The present invention is directed towards methods of removing contaminants from plant-derived pharmaceuticals.

The functional groups of the cannabinoids are: (1) alkanes, (2) alkenes, (3) aromatic rings, (4) phenolic hydroxyls, (5) carboxylic acids, and (6) aryl alkyl ethers. Neutral cannabinoids (i.e., without a carboxylic acid functional group) are insoluble in water.

Without special conditions, the functional groups of the cannabinoids are not subject to attack by most nucleophiles.

The most common alkali metal hydroxides (e.g., alkaline earth hydroxides) are lithium hydroxide, sodium hydroxide, potassium hydroxide, and calcium hydroxide. All of these substances are: (1) inexpensive, (2) readily soluble both in water and the lower molecular weight alcohols (methanol, ethanol, isopropyl alcohol, and n-propanol), and (3) strong nucleophiles and agents of hydrolysis.

Pesticides contain a wide range of functional groups. Most pesticides contain at least one functional group that can be attacked by nucleophiles such as an alkali metal hydroxide in alcoholic solution. Of the 59 pesticides, fungicides, and synergists with levels in *Cannabis* regulated by the State of Oregon, 45 are subject to nucleophilic attack under these conditions, 6 might be, and 8 are not. Once a functional group has been transformed by such a reaction, the biological activity is usually lost.

None of the cannabinoids contain any functional groups that can be attacked by strong nucleophiles such as an alkali metal hydroxide in alcoholic solution.

The present invention provides what is believed to be the best solution to eliminate all hydrolyzable pesticides, which is nearly all pesticides, from *Cannabis* extracts. The method of entirely removing all hydrolyzable pesticides from a given *Cannabis* extract comprises a reaction step, wherein one or more contaminants are reacted with an alkali metal hydroxide solution, followed by an adsorbent based clean-up step to eliminate any pesticide fragments and any remaining pesticides. This desired method is described below, as well as shown in FIGS. 1A-1B.

Figure 1A:
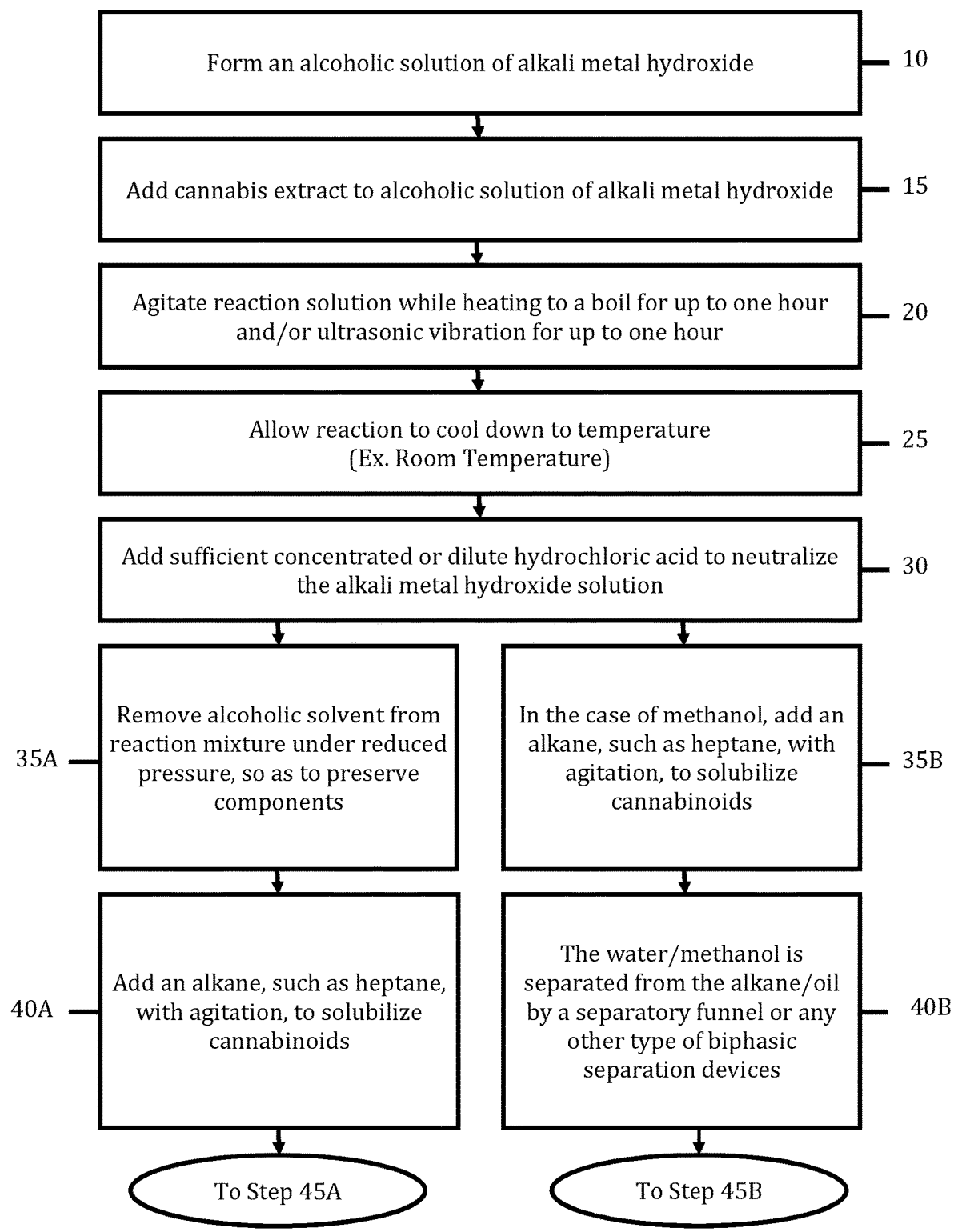
FIGS. 1A-1B depict an exemplary process flowchart showing steps for the removal of contaminants from plant-derived pharmaceuticals.
Figure 1B:
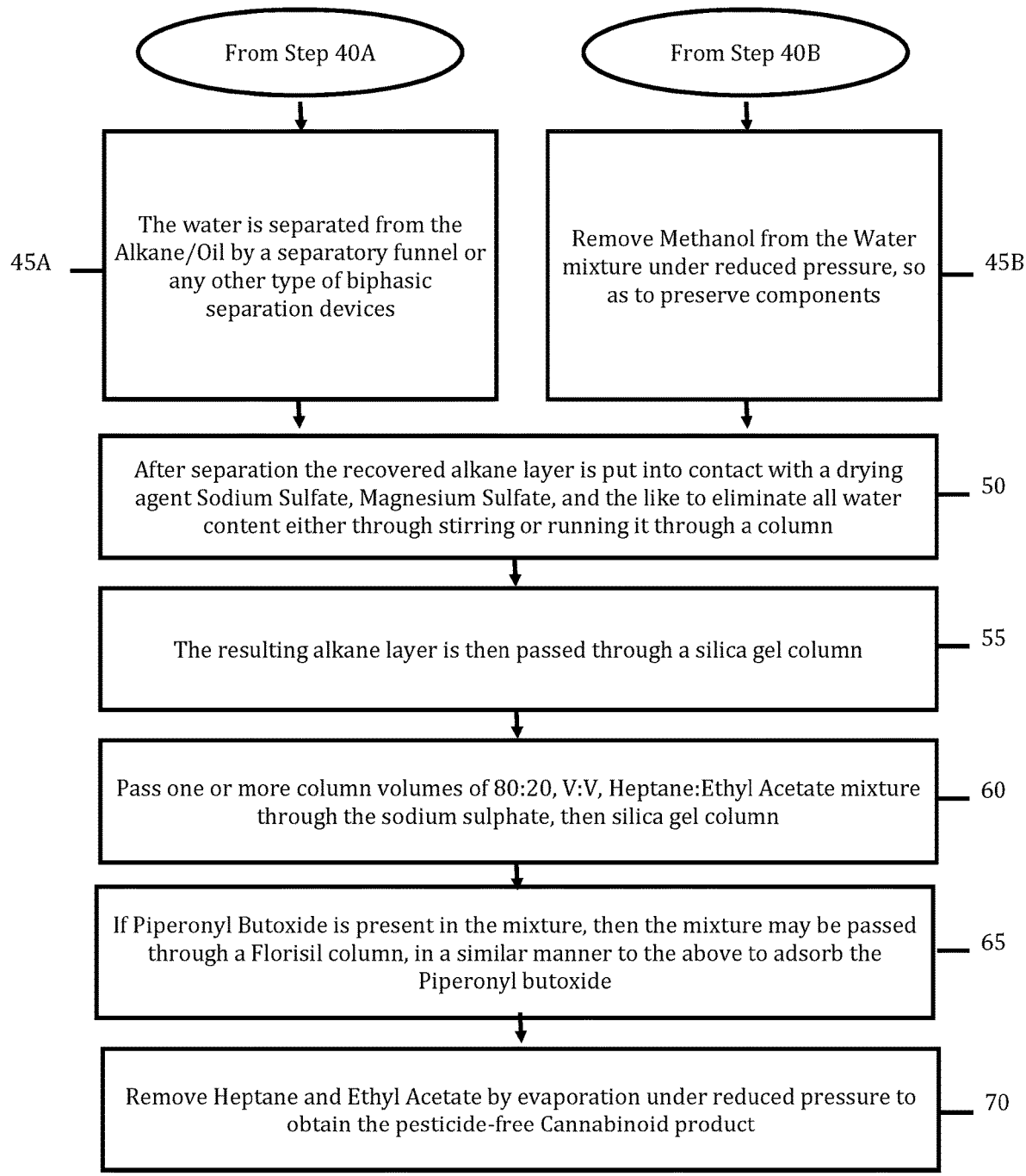

As shown in FIG. 1A, exemplary method 100 of the present invention starts at step 10, wherein an alcoholic solution of alkali metal hydroxide, such as potassium hydroxide, is formed. From step 10, exemplary method 100 proceeds to step 15, wherein a given *Cannabis* extract is added to the alcoholic solution of alkali metal hydroxide. From step 15, exemplary method 100 proceeds to step 20, wherein the resulting reaction solution is agitated with heating (e.g., heating to boil for about an hour) and/or ultrasonic vibration with sufficient molar excess of alkali metal hydroxide for a sufficient time to insure complete reaction, typically for up to an hour or more.

Following complete reaction in step 20, exemplary method 100 proceeds to step 25, wherein the reaction solution is allowed to cool down (e.g., to room temperature). From step 25, exemplary method 100 proceeds to step 30, wherein a neutralizing acid such as a mineral acid (e.g., hydrochloric acid, sulfuric acid, and the like) or a carboxylic acid (e.g., glacial acetic acid and the like) is added to the reaction solution to neutralize the alkaline metal hydroxide and solubilize water-soluble neutralization products such as potassium acetate. The neutralizing acid is added to water and the resulting diluted acid is then added to the mixture. The water serves to absorb the heat of acid-base neutralization. In any case, the neutralizing acid is added in excess to protonate the Cannabinoid acids and the phenolic groups.

From step 30, exemplary method 100 can proceed to step 35A, wherein the alcoholic solvent (i.e., an alcohol solvent other than methanol) is removed by evaporation under reduced pressure, and may be recovered for possible reuse in step 10. If the starting neutralizing acid is concentrated hydrochloric acid diluted with water, then once the alcoholic solvent is removed, an amount of sodium chloride is formed, and a small amount of hydrochloric acid, and the Cannabinoid oil should be present in the resulting reaction mixture. If the starting neutralizing acid is glacial acetic acid diluted with water, then once the alcoholic solvent is removed, an amount of white crystalline potassium acetate is formed, and a small amount of liquid glacial acetic acid, and the Cannabinoid oil should be present in the resulting reaction mixture.

From step 35A, exemplary method 100 proceeds to step 40A, wherein an alkane, such as heptane, is added to the reaction mixture to solubilize cannabinoids within the reaction mixture. From step 40A, exemplary method 100 proceeds to step 45A shown in FIG. 1B, wherein water is separated from the alkane/oil of the reaction mixture via a separatory funnel or any other type of biphasic separation device.

Returning to step 30, if the alcoholic solvent used is methanol, exemplary method 100 can proceed to step 35B, where an alkane solvent (such as pentane, hexane, heptane and the like) is added directly to the reaction mixture since both methanol and water are immiscible with an alkane and the substances of interest are very soluble in the alkane. From step 35B, exemplary method 100 proceeds to step 40B, wherein the water/alcohol is separated from the alkane/oil by a separatory funnel or any other type of biphasic separation devices. From step 40B, exemplary method 100 proceeds to step 45B shown in FIG. 1B, wherein the methanol is removed from the water/methanol mixture by evaporation under reduced pressure for possible reuse in future contaminant-removal cycles (i.e., in step 10). Other alcohols, such as ethanol, isopropanol, n-propanol and so on, are miscible with alkanes so this only works with methanol.

From step 45A or 45B, exemplary method 100 proceeds to step 50, wherein, the recovered alkane/oil layer is put into contact with a drying agent, such as sodium sulfate, magnesium sulfate, and the like, to eliminate all water content. In this step, the powdered drying agent can be added to the recovered alkane/oil layer, agitated, and then filtered off. Alternatively, the drying agent can be added to a chromatographic column and the recovered alkane/oil layer pumped through the filled column.

From step 50, exemplary method 100 proceeds to step 55, wherein the dried alkane/oil layer is passed through a silica gel column. From step 55, exemplary method 100 proceeds to step 60, wherein one or more, typically several, column volumes of a mixture of heptane and ethyl acetate (80:20 v/v) is passed through the silica gel column. The silica gel column (i) allows the non-polar Cannabinoids to pass through unretained, (ii) absorbs any water, (iii) retains fragments of the hydrolyzed pesticides, and (iv) retains unhydrolyzable polar pesticides.

If Piperonyl Butoxide, a non-toxic (i.e., to humans) ingredient commonly added to commercially available insecticides, is believed to be present, exemplary method 100 proceeds from step 60 to step 65, wherein the resulting mixture is passed through a FLORISIL® (magnesium silicate) column to absorb the Piperonyl Butoxide.

It should be noted that the vast majority of commercially available pesticides contain Piperonyl Butoxide because it increases the toxicity of the pesticides to insects. Piperonyl Butoxide is not affected by the above-described hydrolysis step and it elutes from the silica gel column at the same time as the Cannabinoids. Piperonyl Butoxide has a polyether like side chain. FLORISIL® is a tradename for micron sized heat activated (675° C.) magnesium silicate.

From step 65, exemplary method 100 proceeds to step 70, wherein the heptane and ethyl acetate are removed by evaporation under reduced pressure to obtain a pesticide-free Cannabinoid product. If it is known that no Piperonyl Butoxide is present in a given sample, exemplary method 100 may proceed directly to step 70 (i.e., without step 65 shown in FIG. 1B).

The above-described exemplary method 100 has been found to effectively remove many contaminants including, but not limited to, many of the pesticides listed in Table 1 below.

TABLE 1

| | | | | | |
|---|---|---|---|---|---|
| | | Pesticides in Cannabis Regulated by the State of Oregon | | | |
| No. | Pesticide Common Name | Chemical Abstract Services (CAS) Registry | Action Level (ppm) | Chemical Structure | Group Subject To Nucleophilic Attack Present? |
| 1 | Abamectin | 71751-41-2 | 0.5 | 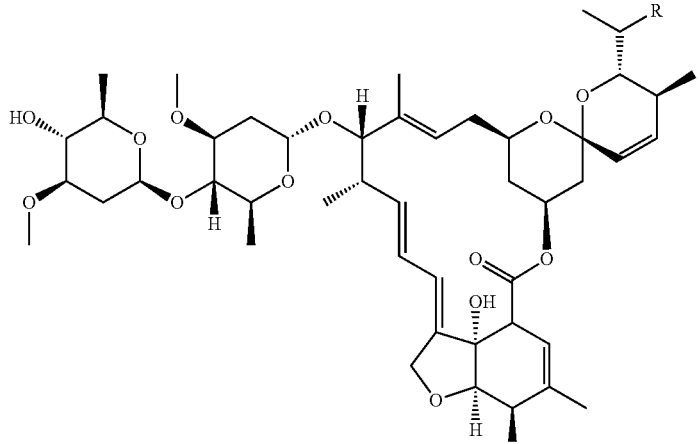<br>Avermectin $B_{1a}$<br>$R = CH_2CH_3$<br>Avermectin $B_{1b}$<br>$R = CH_3$ | Yes |
| 2 | Acephate | 30560-19-1 | 0.4 | 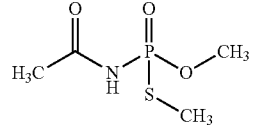 | Yes |
| 3 | Acequinocyl | 57960-19-7 | 2 | 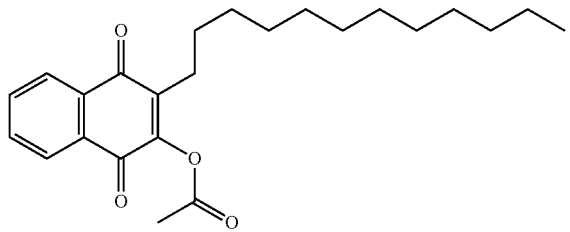 [SMILES: CCCCCCCCCCCCC1=C(OC(C)=O)C(=O)c2ccccc2C1=O] | Yes |
| 4 | Acetamiprid | 135410-20-7 | 0.2 | 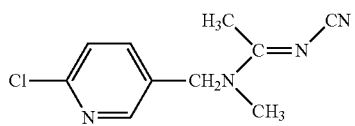 | Yes |

TABLE 1-continued

Pesticides in Cannabis Regulated by the State of Oregon

| No. | Pesticide Common Name | Chemical Abstract Services (CAS) Registry | Action Level (ppm) | Chemical Structure | Group Subject To Nucleophilic Attack Present? |
|---|---|---|---|---|---|
| 5 | Aldicarb | 116-06-3 | 0.4 | 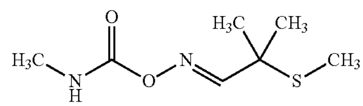 | Yes |
| 6 | Azoxystrobin | 131860-33-8 | 0.2 | 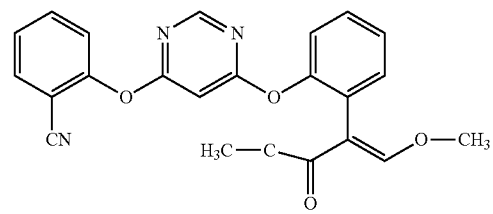 [SMILES: CCC(=O)/C(=C/OC)c1ccccc1Oc1cc(Oc2ccccc2C#N)ncn1] | Yes |
| 7 | Bifenazate | 149877-41-8 | 0.2 | 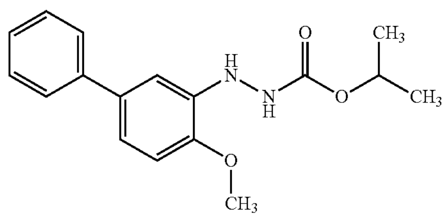 [SMILES: COc1ccc(-c2ccccc2)cc1NNC(=O)OC(C)C] | Yes |
| 8 | Bifenthrin | 82657-04-3 | 0.2 | 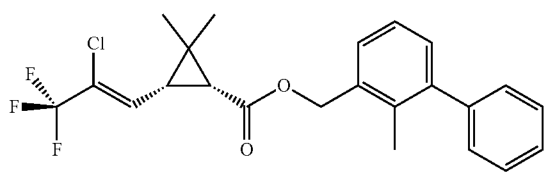 | Yes |
| 9 | Boscalid | 188425-85-6 | 0.4 | 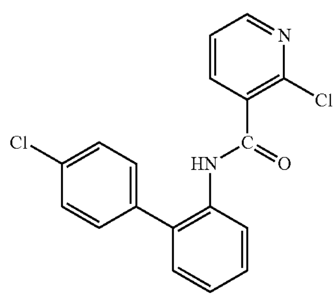 [SMILES: O=C(Nc1ccccc1-c1ccc(Cl)cc1)c1cccnc1Cl] | No |
| 10 | Carbaryl | 63-25-2 | 0.2 | 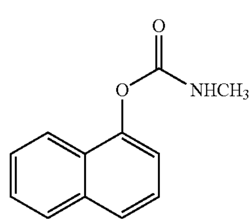 [SMILES: CNC(=O)Oc1cccc2ccccc12] | Yes |
| 11 | Carbofuran | 1563-66-2 | 0.2 | 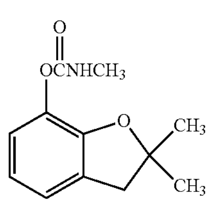 | Yes |

TABLE 1-continued

Pesticides in Cannabis Regulated by the State of Oregon

| No. | Pesticide Common Name | Chemical Abstract Services (CAS) Registry | Action Level (ppm) | Chemical Structure | Group Subject To Nucleophilic Attack Present? |
|---|---|---|---|---|---|
| 12 | Chlorantraniliprole | 500008-45-7 | 0.2 | 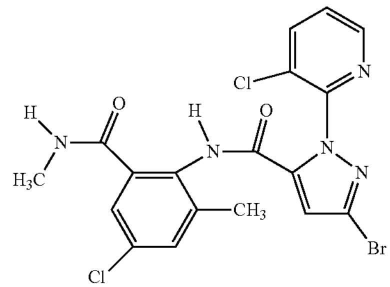 [SMILES: CNC(=O)c1cc(Cl)cc(C)c1NC(=O)c1cc(Br)nn1-c1ncccc1Cl] | Yes |
| 13 | Chlorfenapyr | 122453-73-0 | 1 | 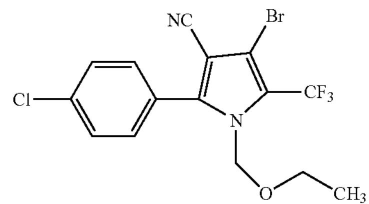 [SMILES: CCOCn1c(-c2ccc(Cl)cc2)c(C#N)c(Br)c1C(F)(F)F] | No |
| 14 | Chlorpyrifos | 2921-88-2 | 0.2 | 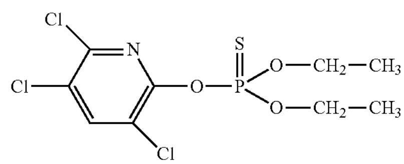 [SMILES: CCOP(=S)(OCC)Oc1nc(Cl)c(Cl)cc1Cl] | Yes |
| 15 | Clofentezine | 74115-24-5 | 0.2 | 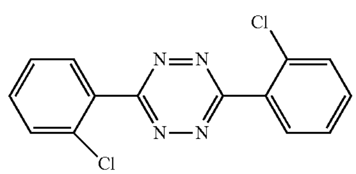 [SMILES: Clc1ccccc1-c1nnc(-c2ccccc2Cl)nn1] | Maybe |
| 16 | Cyfluthrin | 68359-37-5 | 1 | 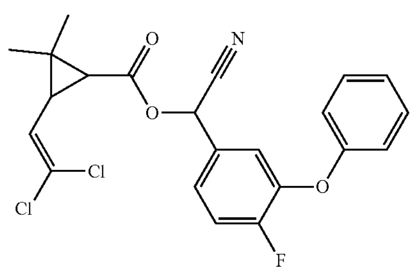 [SMILES: CC1(C)C(C=C(Cl)Cl)C1C(=O)OC(C#N)c1ccc(F)c(Oc2ccccc2)c1] | Yes |
| 17 | Cypermethrin | 52315-07-8 | 1 | 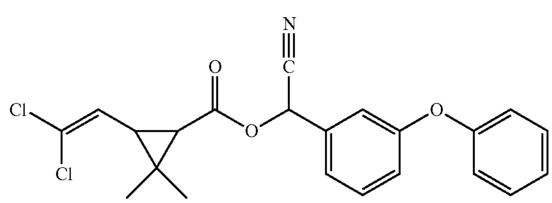 [SMILES: CC1(C)C(C=C(Cl)Cl)C1C(=O)OC(C#N)c1cccc(Oc2ccccc2)c1] | Yes |
| 18 | Daminozide | 1596-84-5 | 1 | 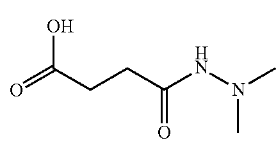 | Yes |

TABLE 1-continued
Pesticides in Cannabis Regulated by the State of Oregon
| No. | Pesticide Common Name | Chemical Abstract Services (CAS) Registry | Action Level (ppm) | Chemical Structure | Group Subject To Nucleophilic Attack Present? |
|---|---|---|---|---|---|
| 19 | DDVP (Dichlorvos) | 62-73-7 | 0.1 | 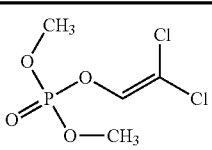 | Yes |
| 20 | Diazinon | 333-41-5 | 0.2 | 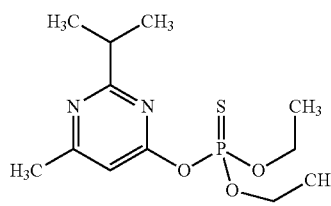 | Yes |
| 21 | Dimethoate | 60-51-5 | 0.2 | 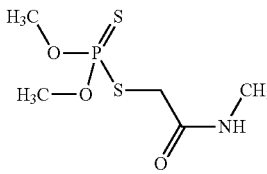 | Yes |
| 22 | Ethoprophos | 13194-48-4 | 0.2 | 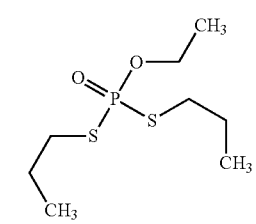 | Yes |
| 23 | Etofenprox | 80844-07-1 | 0.4 | 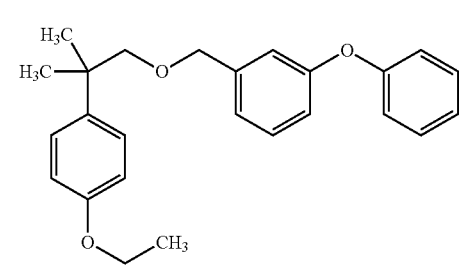 [SMILES: CCOc1ccc(C(C)(C)COCc2cccc(Oc3ccccc3)c2)cc1] | No |
| 24 | Etoxazole | 153233-91-1 | 0.2 | 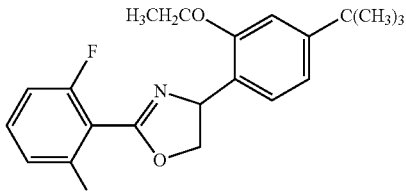 | No |
| 25 | Fenoxycarb | 72490-01-8 | 0.2 | 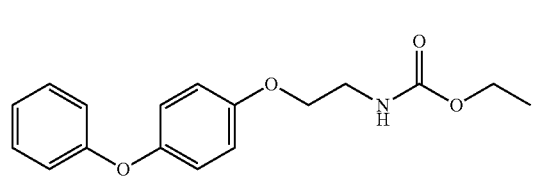 [SMILES: CCOC(=O)NCCOc1ccc(Oc2ccccc2)cc1] | Yes |

TABLE 1-continued

Pesticides in Cannabis Regulated by the State of Oregon

| No. | Pesticide Common Name | Chemical Abstract Services (CAS) Registry | Action Level (ppm) | Chemical Structure | Group Subject To Nucleophilic Attack Present? |
|---|---|---|---|---|---|
| 26 | Fenpyroximate | 134098-61-6 | 0.4 | 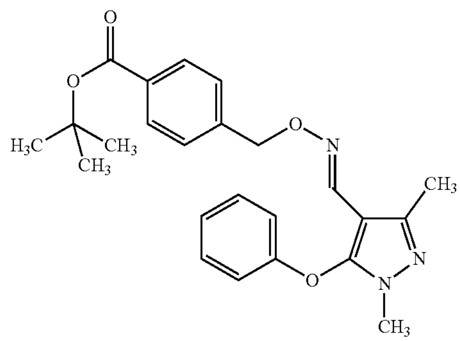 [SMILES: Cc1nn(C)c(Oc2ccccc2)c1/C=N/OCc1ccc(C(=O)OC(C)(C)C)cc1] | Yes |
| 27 | Fipronil | 120068-37-3 | 0.4 | 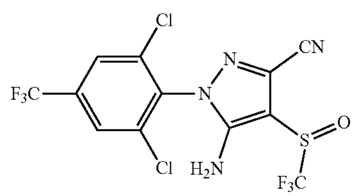 [SMILES: N#Cc1nn(-c2c(Cl)cc(C(F)(F)F)cc2Cl)c(N)c1S(=O)C(F)(F)F] | Yes |
| 28 | Flonicamid | 158062-67-0 | 1 | 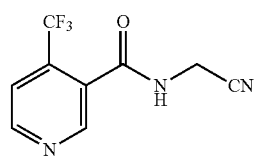 [SMILES: N#CCNC(=O)c1cnccc1C(F)(F)F] | May-be |
| 29 | Fludioxonil | 131341-86-1 | 0.4 | 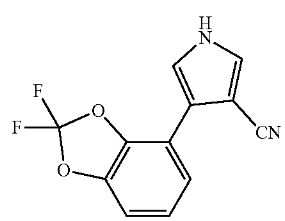 [SMILES: N#Cc1c[nH]cc1-c1cccc2c1OC(F)(F)O2] | No |
| 30 | Hexythiazox | 78587-05-0 | 1 | 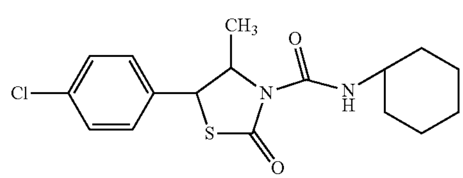 [SMILES: CC1C(c2ccc(Cl)cc2)SC(=O)N1C(=O)NC1CCCCC1] | Yes |
| 31 | Imazalil | 35554-44-0 | 0.2 | 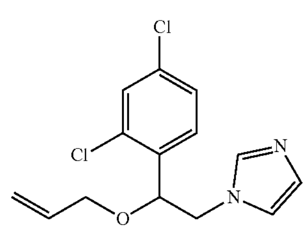 [SMILES: C=CCOC(Cn1ccnc1)c1ccc(Cl)cc1Cl] | May-be |

TABLE 1-continued

Pesticides in Cannabis Regulated by the State of Oregon

| No. | Pesticide Common Name | Chemical Abstract Services (CAS) Registry | Action Level (ppm) | Chemical Structure | Group Subject To Nucleophilic Attack Present? |
|---|---|---|---|---|---|
| 32 | Imidacloprid | 138261-41-3 | 0.4 | 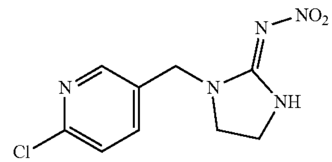 [SMILES: O=[N+]([O-])/N=C1\NCCN1Cc1ccc(Cl)nc1] | Yes |
| 33 | Kresoxim-methyl | 143390-89-0 | 0.4 | 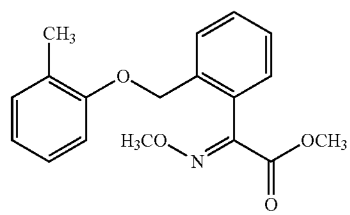 [SMILES: CO/N=C(/C(=O)OC)c1ccccc1COc1ccccc1C] | Yes |
| 34 | Malathion | 121-75-5 | 0.2 | 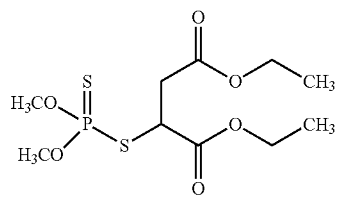 [SMILES: CCOC(=O)CC(SP(=S)(OC)OC)C(=O)OCC] | Yes |
| 35 | Metalaxyl | 57837-19-1 | 0.2 | 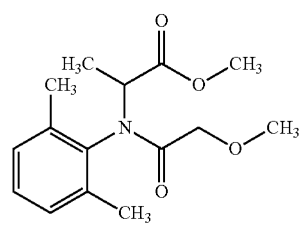 [SMILES: COCC(=O)N(c1c(C)cccc1C)C(C)C(=O)OC] | Yes |
| 36 | Methiocarb | 2032-65-7 | 0.2 | 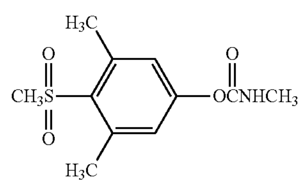 | Yes |
| 37 | Methomyl | 16752-77-5 | 0.4 | 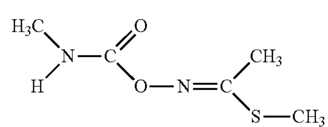 | Yes |
| 38 | Methyl parathion | 298-00-0 | 0.2 | 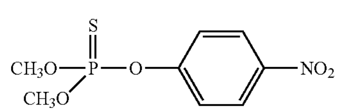 | Yes |
| 39 | MGK-264 | 113-48-4 | 0.2 | 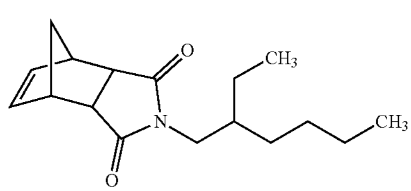 [SMILES: CCCCC(CC)CN1C(=O)C2C3C=CC(C3)C2C1=O] | May-be |

TABLE 1-continued
Pesticides in Cannabis Regulated by the State of Oregon
| No. | Pesticide Common Name | Chemical Abstract Services (CAS) Registry | Action Level (ppm) | Chemical Structure | Group Subject To Nucleophilic Attack Present? |
|---|---|---|---|---|---|
| 40 | Myclobutanil | 88671-89-0 | 0.2 | 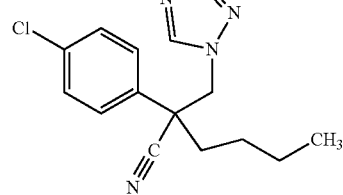 | Yes |
| 41 | Naled | 300-76-5 | 0.5 | 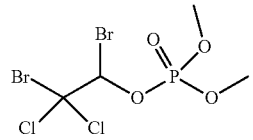 | Yes |
| 42 | Oxamyl | 23135-22-0 | 1 | 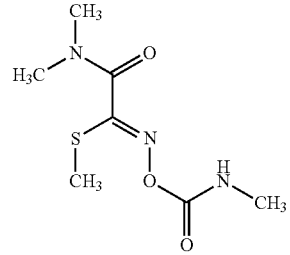 | Yes |
| 43 | Paclobutrazol | 76738-62-0 | 0.4 | 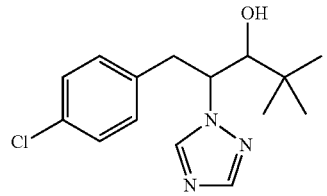 [SMILES: CC(C)(C)C(O)C(Cc1ccc(Cl)cc1)n1cncn1] | Maybe |
| 44 | Permethrins | 52645-53-1 | 0.2 | 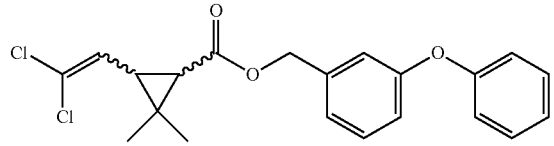 [SMILES: CC1(C)C(C=C(Cl)Cl)C1C(=O)OCc1cccc(Oc2ccccc2)c1] | Yes |
| 45 | Phosmet | 732-11-6 | 0.2 | 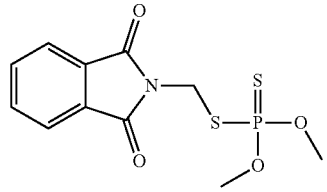 [SMILES: COP(=S)(OC)SCN1C(=O)c2ccccc2C1=O] | Yes |
| 46 | Piperonyl butoxide | 51-03-6 | 2 | 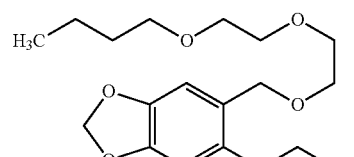 | No |

TABLE 1-continued

Pesticides in Cannabis Regulated by the State of Oregon

| No. | Pesticide Common Name | Chemical Abstract Services (CAS) Registry | Action Level (ppm) | Chemical Structure | Group Subject To Nucleophilic Attack Present? |
|---|---|---|---|---|---|
| 47 | Prallethrin | 23031-36-9 | 0.2 | 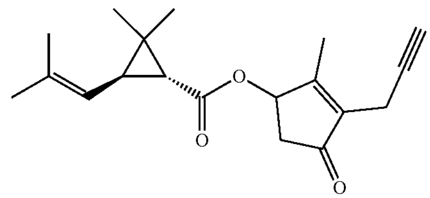 [SMILES: C#CCC1=C(C)C(OC(=O)[C@@H]2[C@@H](C=C(C)C)C2(C)C)CC1=O] | Yes |
| 48 | Propiconazole | 60207-90-1 | 0.4 | 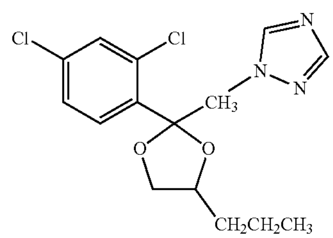 | No |
| 49 | Propoxur | 114-26-1 | 0.2 | 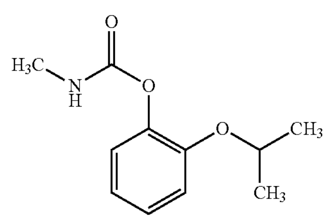 | Yes |
| 50 | Pyrethrins | 8003-34-7 | 1 | 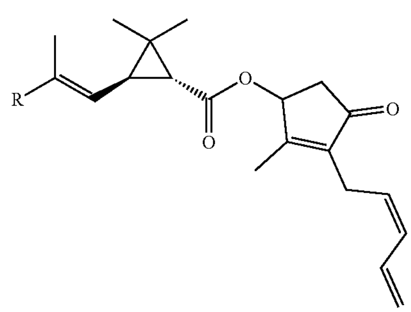 | Yes |
| 51 | Pyridaben | 96489-71-3 | 0.2 | 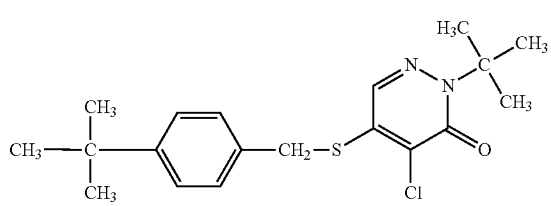 [SMILES: CC(C)(C)c1ccc(CSc2cnn(C(C)(C)C)c(=O)c2Cl)cc1] | Yes |

TABLE 1-continued
Pesticides in Cannabis Regulated by the State of Oregon
| No. | Pesticide Common Name | Chemical Abstract Services (CAS) Registry | Action Level (ppm) | Chemical Structure | Group Subject To Nucleophilic Attack Present? |
|---|---|---|---|---|---|
| 52 | Spinosad | 168316-95-8 | 0.2 | 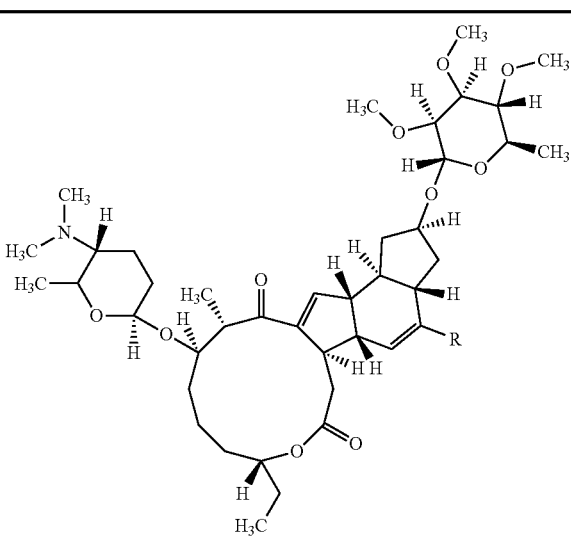<br>R = H, CH$_3$ | Yes |
| 53 | Spiromesifen | 283594-90-1 | 0.2 | 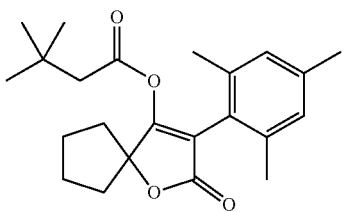 [SMILES: Cc1cc(C)c(C2=C(OC(=O)CC(C)(C)C)C3(CCCC3)OC2=O)c(C)c1] | Yes |
| 54 | Spirotetramat | 203313-25-1 | 0.2 | 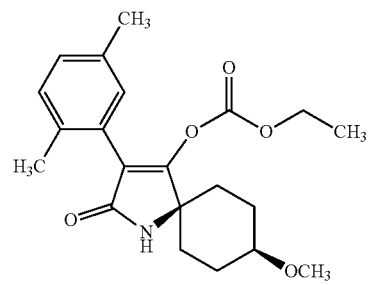 [SMILES: CCOC(=O)OC1=C(c2cc(C)ccc2C)C(=O)N[C@]12CC[C@@H](OC)CC2] | Yes |
| 55 | Spiroxamine | 118134-30-8 | 0.4 | 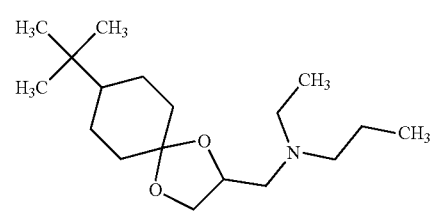 [SMILES: CCCN(CC)CC1COC2(CCC(C(C)(C)C)CC2)O1] | No |
| 56 | Tebuconazole | 80443-41-0 | 0.4 | 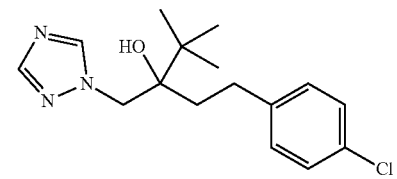 [SMILES: CC(C)(C)C(O)(CCc1ccc(Cl)cc1)Cn1cncn1] | May-be |

TABLE 1-continued

Pesticides in Cannabis Regulated by the State of Oregon

| No. | Pesticide Common Name | Chemical Abstract Services (CAS) Registry | Action Level (ppm) | Chemical Structure | Group Subject To Nucleophilic Attack Present? |
|---|---|---|---|---|---|
| 57 | Thiacloprid | 111988-49-9 | 0.2 | 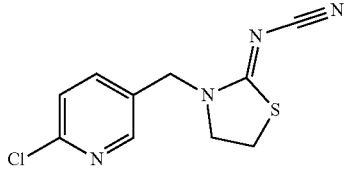 [SMILES: N#C/N=C1\SCCN1Cc1ccc(Cl)nc1] | Yes |
| 58 | Thiamethoxam | 153719-23-4 | 0.2 | 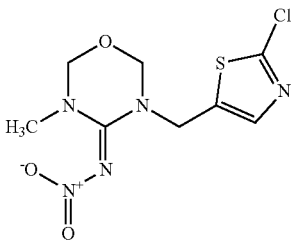 | Yes |
| 59 | Trifloxystrobin | 141517-21-7 | 0.2 | 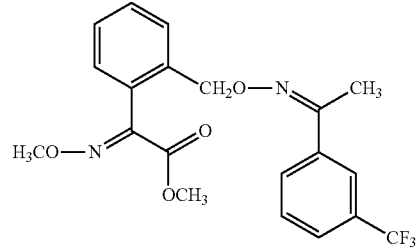 | Yes |

Further, the above-described exemplary method 100 has been found to effectively produce essentially pesticide-free cannabinoids including, but not limited to, many of the cannabinoids listed in Tables 2 and 3 below.

TABLE 2

Cannabinoids

| Class | Substance | Common Abbreviation | Water Soluble? |
|---|---|---|---|
| Cannabichromene | Cannabichromene | CBC | No |
| Cannabichromene | Cannabichromenic acid | CBCA | Yes |
| Cannabichromene | Cannabichromevarin | CBCV | No |
| Cannabichromene | Cannabichromevarinic acid | CBCVA | No |
| Cannabichromene | Cannabicyclols | | No |
| Cannabichromene | Cannabicyclol | CBL | No |
| Cannabichromene | Cannabicyclolic acid | CBLA | Yes |
| Cannabichromene | Cannabicyclovarin | CBLV | No |
| Cannabidiols | Cannabidiol | CBD | No |
| Cannabidiols | Cannabidiol monomethylether | CBDM | No |
| Cannabidiols | Cannabidiolic acid | CBDA | No |
| Cannabidiols | Cannabidiorcol | CBD-C1 | No |
| Cannabidiols | Cannabidivarin | CBDV | No |
| Cannabidiols | Cannabidivarinic acid | CBDVA | Yes |
| Cannabielsoins | Cannabielsoic acid B | CBEA-B | No |
| Cannabielsoins | Cannabielsoin | CBE | No |
| Cannabielsoins | Cannabielsoin acid A | CBEA-A | No |
| Cannabigerols | Cannabigerol | CBG | No |
| Cannabigerols | Cannabigerol monomethylether | CBGM | No |
| Cannabigerols | Cannabigerolic acid | CBGA | Yes |
| Cannabigerols | Cannabigerolic acid monomethylether | CBGAM | Yes |
| Cannabigerols | Cannabigerovarin | CBGV | No |
| Cannabigerols | Cannabigerovarinic acid | CBGVA | Yes |

TABLE 2-continued

Cannabinoids

| Class | Substance | Common Abbreviation | Water Soluble? |
|---|---|---|---|
| Cannabinols and cannabinodiols | Cannabinodiol | CBND | No |
| Cannabinols and cannabinodiols | Cannabinodivarin | CBVD | No |
| Cannabinols and cannabinodiols | Cannabinol | CBN | No |
| Cannabinols and cannabinodiols | Cannabinol methylether | CBNM | No |
| Cannabinols and cannabinodiols | Cannabinol-C2 | CBN-C2 | No |
| Cannabinols and cannabinodiols | Cannabinol-C4 | CBN-C4 | No |
| Cannabinols and cannabinodiols | Cannabinolic acid | CBNA | Yes |
| Cannabinols and cannabinodiols | Cannabiorcool | CBN-C1 | No |
| Cannabinols and cannabinodiols | Cannabivarin | CBV | No |
| Cannabitriols | 10-Ethoxy-9-hydroxy-delta-6a-tetrahydrocannabinol | | No |
| Cannabitriols | 8,9-Dihydroxy-delta-6a-tetrahydrocannabinol | | No |
| Cannabitriols | Cannabitriol | CBT | No |
| Cannabitriols | Cannabitriolvarin | CBTV | No |
| Delta-8-tetrahydrocannabinols | Delta-8-tetrahydrocannabinol | Δ8-THC | No |
| Delta-8-tetrahydrocannabinols | Delta-8-tetrahydrocannabinolic acid | Δ8-THCA | Yes |
| Delta-9-tetrahydrocannabinols | Delta-9-tetrahydrocannabinol | THC | No |
| Delta-9-tetrahydrocannabinols | Delta-9-tetrahydrocannabinol-C4 | THC-C4 | No |
| Delta-9-tetrahydrocannabinols | Delta-9-tetrahydrocannabinolic acid A | THCA-A | Yes |
| Delta-9-tetrahydrocannabinols | Delta-9-tetrahydrocannabinolic acid B | THCA-B | Yes |
| Delta-9-tetrahydrocannabinols | Delta-9-tetrahydrocannabinolic acid-C4 | THCA-C4 | Yes |
| Delta-9-tetrahydrocannabinols | Delta-9-tetrahydrocannabiorcol | THC-C1 | No |
| Delta-9-tetrahydrocannabinols | Delta-9-tetrahydrocannabiorcolic acid | THCA-C1 | Yes |
| Delta-9-tetrahydrocannabinols | Delta-9-tetrahydrocannabivarin | THCV | No |
| Delta-9-tetrahydrocannabinols | Delta-9-tetrahydrocannabivarinic acid | THCVA | Yes |
| Miscellaneous cannabinoids | 10-Oxo-delta-6a-tetrahydrocannabinol | OTHC | No |
| Miscellaneous cannabinoids | Cannabichromanon | CBCF | No |
| Miscellaneous cannabinoids | Cannabifuran | CBF | No |
| Miscellaneous cannabinoids | Cannabiglendol | | No |
| Miscellaneous cannabinoids | Cannabiripsol | CBR | No |
| Miscellaneous cannabinoids | Cannbicitran | CBT | No |
| Miscellaneous cannabinoids | Dehydrocannabifuran | DCBF | No |
| Miscellaneous cannabinoids | Delta-9-cis-tetrahydrocannabinol | cis-THC | No |
| Miscellaneous cannabinoids | Tryhydroxy-delta-9-tetrahydrocannabinol | triOH-THC | No |

TABLE 3

Cannabinoids with Carboxylic Acids and Corresponding Decarboxylated Products

| | | | |
|---|---|---|---|
| Cannabigerolic acid | CBGA | Cannabigerol | CBG |
| Δ9-tetrahydrocannabinolic acid | THCA | Δ9-tetrahydrocannabinol | THC |
| Cannabidiolic acid | CBDA | Cannabidiol | CBD |

TABLE 3-continued

Cannabinoids with Carboxylic Acids and Corresponding Decarboxylated Products

| | | | |
|---|---|---|---|
| Cannabichromenenic acid | CBCA | Cannabichromene | CBC |
| Cannabigerovarinic acid | CBGVA | Cannabigerivarin | CBGV |
| Tetrahydrocanabivarinic acid | THCVA | Tetrahydrocannabivarin | THCV |
| Cannabidivarinic acid | CBDVA | Cannabidivarin | CBDV |
| Cannabichromevarinic acid | CBCVA | Cannabichromevarin | CBCV |

II. Plant-Derived Pharmaceuticals

The present invention is also directed to plant-derived pharmaceuticals formed via the herein-described contaminant removal methods. The plant-derived pharmaceuticals include, but are not limited to, the cannabinoids listed in Tables 2 and 3 above.

III. Methods of Using Plant-Derived Pharmaceuticals

The present invention is also directed towards methods of using plant-derived pharmaceuticals formed via the herein-described contaminant removal methods. Methods of using the plant-derived pharmaceuticals formed via the herein-described contaminant removal methods include, but are not limited to, methods of treating a patient with a disease or disorder, wherein the treatment comprises administering an effective amount of one or more of the plant-derived pharmaceuticals to the patient.

In one exemplary embodiment, the method of treated a patient with a disease or disorder comprises administering an effective amount of one or more pesticide-free cannabinoids, such as one or more of the cannabinoids shown in Tables 2 and 3, to the patient. A number of diseases and/or disorders may be treated using Cannabinoids including, but not limited to, (1) anxiety (i.e., to reduce anxiety), (2) inflammation (i.e., to reduce inflammation), (3) pain (i.e., to relief pain), (4) nausea and vomiting caused by chemotherapy (i.e., to reduce nausea and vomiting), (5) cancer (i.e., to kill cancer cells and slow tumor growth), (6) multiple sclerosis (i.e., to relax tight muscles in people with multiple sclerosis), and (7) appetite and weight gain (i.e., to stimulate appetite and improve weight gain in people with cancer and AIDS).

The present invention will be further described in the following additional embodiments, examples, and claims.

Additional Embodiments

Methods of Removing Contaminants From Plant-Derived Pharmaceuticals

1. A method of removing contaminants from a plant-derived pharmaceutical, said method comprising: reacting one or more contaminants within a plant-derived extract with an alkali metal hydroxide in polar solvent to form one or more contaminant by-products in a reaction mixture; and separating the one or more contaminant by-products from the plant-derived extract so as to obtain a contaminant-reduced, plant-derived extract.

2. The method of embodiment 1, wherein the one or more contaminants comprise one or more pesticides, one or more herbicides, one or more fungicides, or any combination thereof.

3. The method of embodiment 1 or 2, wherein the one or more contaminants comprise one or more hydrolyzable pesticides.

4. The method of any one of embodiments 1 to 3, wherein the alkali metal hydroxide comprises lithium hydroxide, sodium hydroxide, potassium hydroxide, calcium hydroxide, or ionic liquids such as 1-ethyl-3-methylimidazolium hydroxide.

5. The method of any one of embodiments 1 to 4, wherein the alkali metal hydroxide comprises potassium hydroxide.

6. The method of any one of embodiments 1 to 5, wherein the polar solvent comprises methanol, ethanol, n-propanol, isopropanol, butanol, dimethyl sulfoxide, dimethylformamide, or any combination thereof.

7. The method of any one of embodiments 1 to 6, wherein the polar solvent comprises methanol.

8. The method of any one of embodiments 1 to 7, further comprising: forming a polar solvent solution comprising the alkali metal hydroxide in the polar solvent, wherein the alkali metal hydroxide is present in the polar solvent at a concentration of from about 0.125 grams (g) to 0.5 g of alkali metal hydroxide per milliliter (ml) of polar solvent.

9. The method of any one of embodiments 1 to 8, wherein said reacting step comprises: adding the plant-derived extract to the alkali metal hydroxide in the polar solvent to form the reaction mixture; and agitating the reaction mixture with mixing while (i) heating the reaction mixture to boiling for a period of time up to about one hour, (ii) ultrasonically vibrating the reaction mixture for a period of time up to about one hour, or (iii) both (i) and (ii).

10. The method of embodiment 9, wherein said method further comprises, following said agitating step: allowing the reaction mixture to cool down to below about 40° C.

11. The method of any one of embodiments 1 to 10, wherein said reacting step further comprises: following a cooling down step, adding a neutralizing acid to the reaction mixture, wherein the neutralizing acid comprises organic carboxylic acids such as glacial acetic acid, or a dilute mineral acid such as hydrochloric acid, sulfuric acid, nitric acid, and the like.

12. The method of embodiment 11, wherein the neutralizing acid comprises glacial acetic acid.

13. The method of embodiment 11 or 12, wherein the neutralizing acid is added in an amount of from about 6.0 ml to about 18.0 ml.

14. The method of any one of embodiments 11 to 13, wherein the neutralizing acid is added in an amount of about 8.0 ml (e.g., 130 mM of glacial acetic acid).

15. The method of any one of embodiments 1 to 14, wherein said separating step comprises: evaporating the polar solvent from the reaction mixture under reduced pressure so as to result in a polar solvent-free reaction mixture comprising (i) crystalline alkali metal acetate, (ii) neutralizing acid, and (iii) the plant-derived extract.

16. The method of embodiment 15, wherein said separating step further comprises: adding a first alkane to the polar solvent-free reaction mixture so as to form a non-aqueous liquid phase.

17. The method of embodiment 16, wherein from about 30 ml to about 120 ml of water is added to the polar solvent-free reaction mixture.

18. The method of embodiment 16 or 17, wherein about 40 ml of water is added to the polar solvent-free reaction mixture.

19. The method of any one of embodiments 16 to 18, wherein from about 30 ml to about 120 ml of the first alkane is added to the polar solvent-free reaction mixture.

20. The method of any one of embodiments 16 to 19, wherein about 40 ml of the first alkane is added to the polar solvent-free reaction mixture.

21. The method of any one of embodiments 16 to 20, wherein the first alkane is butane, pentane, cyclopentane, hexane, cyclohexane, heptane, octane, isooctane, or any combination thereof.

22. The method of any one of embodiments 16 to 21, wherein the first alkane is heptane.

23. The method of any one of embodiments 16 to 22, further comprising: agitating the aqueous liquid phase and the non-aqueous liquid phase so as to dissolve (1)(i) the crystalline alkali metal acetate, and (ii) the neutralizing acid in the aqueous liquid phase, and (2) the plant-derived extract in the non-aqueous liquid phase.

24. The method of any one of embodiments 16 to 23, further comprising: introducing the aqueous liquid phase and the non-aqueous liquid phase into a separatory funnel so as to form an upper non-aqueous liquid phase and a lower aqueous liquid phase; and separating the lower aqueous liquid phase from the upper non-aqueous liquid phase.

25. The method of embodiment 24, further comprising: passing the upper non-aqueous liquid phase through one or more columns with each column comprising one or more adsorbents; and collecting an effluent exiting the one or more columns.

26. The method of embodiment 25, wherein the one or more adsorbents comprise magnesium silicate (e.g., FLORISIL® adsorbent), activated alumina, magnesium salt of activated alumina, silica, bonded phase silica, polymeric non-ionic reversed phase resins, or any combination thereof.

27. The method of embodiment 25 or 26, wherein the one or more adsorbents comprise silica gel in a first column.

28. The method of any one of embodiments 25 to 27, wherein the one or more adsorbents comprise magnesium silicate (e.g., FLORISIL® adsorbent) in a second column.

29. The method of any one of embodiments 24 to 28, wherein each of the one or more columns comprises from about 25 g to about 60 g of the one or more adsorbents.

30. The method of any one of embodiments 24 to 29, wherein each of the one or more columns comprises about 40 g of the one or more adsorbents.

31. The method of any one of embodiments 24 to 30, further comprising: passing one or more column volumes of a rinse mixture through the one or more columns (e.g., an initial weak solvent (e.g., one or more second alkanes such as heptane) with or without some small percentage (e.g., 1-20 wt %) of a stronger solvent (e.g., methanol, ethanol, isopropanol, n-propanol, ethyl acetate, acetone, dichloromethane, chloroform, toluene, and the like) to reduce collection volume but without eluting any residual undesirable non-Cannabinoid substances); and collecting the effluent exiting the one or more columns.

32. The method of embodiment 31, wherein the one or more column volumes comprises from about 40 ml to about 180 ml of the rinse mixture.

33. The method of embodiment 31 or 32, wherein the one or more column volumes comprises about 120 ml of the rinse mixture.

34. The method of any one of embodiments 31 to 33, wherein the second alkane and the ethyl acetate are present, by volume, at a ratio of 80:20 v/v.

35. The method of any one of embodiments 31 to 34, wherein the second alkane comprises heptane.

36. The method of any one of embodiments 25 to 35, further comprising: evaporating the effluent under reduced pressure so as to (1) remove one or more of: (i) the first alkane, (ii) the weak solvent (e.g., second alkane), and (iii) the stronger solvent (e.g., ethyl acetate), and (2) result in the contaminant-reduced plant-derived extract.

37. The method of any one of embodiments 1 to 36, further comprising: testing the contaminant-reduced plant-derived extract for possible detectable levels of one or more contaminants.

38. The method of any one of embodiments 1 to 37, wherein from about 5 g to about 25 g of the plant-derived extract is reacted with the alkali metal hydroxide in the alcohol.

39. The method of any one of embodiments 1 to 38, wherein about 10 g of the plant-derived extract is reacted with the alkali metal hydroxide in the alcohol.

40. The method of any one of embodiments 1 to 39, wherein the plant-derived extract is a *Cannabis*-derived extract.

41. The method of any one of embodiments 1 to 40, wherein the contaminant-reduced plant-derived extract comprises one or more cannabinoids.

Contaminant-Reduced Plant-Derived Pharmaceuticals

42. A contaminant-reduced plant-derived extract formed by the method of any one of embodiments 1 to 41.

Methods of Using Contaminant-Reduced Plant-Derived Pharmaceuticals

43. A method of using the contaminant-reduced plant-derived extract formed by the method of any one of embodiments 1 to 41, said method comprising: treating a patient suffering from a disease or disorder by administering an effective amount of the contaminant-reduced plant-derived extract to the patient.

44. The method of embodiment 43, wherein the effective amount of the contaminant-reduced plant-derived extract is orally provided to the patient.

45. The method of embodiment 43 or 44, wherein the effective amount of the contaminant-reduced plant-derived extract is intravenously provided to the patient.

46. The method of any one of embodiments 43 to 45, wherein the disease or disorders comprises (1) anxiety (i.e., to reduce anxiety), (2) inflammation (i.e., to reduce inflammation), (3) pain (i.e., to relief pain), (4) nausea and vomiting caused by chemotherapy (i.e., to reduce nausea and vomiting), (5) cancer (i.e., to kill cancer cells and slow tumor growth), (6) multiple sclerosis (i.e., to relax tight muscles in people with multiple sclerosis), (7) appetite and weight gain (i.e., to stimulate appetite and improve weight gain in people with cancer and AIDS), or any combination thereof.

The present invention is further illustrated by the following example, which is not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Methods of removing contaminants from *Cannabis*-derived extracts were conducted as follows:
1) Add 5.0 g of KOH (90 mM) pellets to 40 ml of methanol and dissolve;
2) Add 10 g of *Cannabis* extract to the KOH/methanol mixture and agitate until the *Cannabis* extract dissolves;
3) With agitation, either (i) heat to boiling for 1 hour, or (ii) add ultrasonic vibrations for 1 hour;
4) Cool down;
5) Add 8 ml Glacial Acetic Acid (130 mM);
6) Evaporate methanol under reduced pressure and recover the methanol so as to produce (i) a relatively large amount of white crystalline potassium acetate, (ii) a relatively small amount of liquid glacial acetic acid, and (iii) the cannabinoid oil;
7) Add 40 ml of water to the mixture of (i) white crystalline potassium acetate, (ii) liquid glacial acetic acid, and (iii) the cannabinoid oil;
8) Add 40 ml of heptane to the mixture and agitate until the potassium acetate and the glacial acetic acid are dissolved in the aqueous lower layer and the cannabinoid oil in the heptane upper layer;
9) Use a separatory funnel to recover the upper heptane layer; 10) Pass the recovered upper heptane layer through a column of 40 g of silica gel;
11) Pass 120 ml of heptane:ethyl acetate mixture (80:20, v/v) through the silica gel column;
12) Evaporate under reduced pressure the heptane/ethyl acetate from the mixture until only the *Cannabis* extract is left; and
13) Test the *Cannabis* extract for pesticide levels.

For one exemplary lot, eight pesticides within the original *Cannabis* extract were removed to undetectable levels as shown in Table 4 below.

TABLE 4

Select Pesticide Content In A *Cannabis* Extract Prior to and After Processing Using the Method of Example 1

| Pesticide | Level In Organic Extract | Level In Treated Extract |
|---|---|---|
| Bifenazate | 41.0 ppm | Not Detectable |
| Bifenthrin | 1.04 ppm | Not Detectable |
| Boscalid | 1.96 ppm | Not Detectable |
| Fenpyroximate | 2.86 ppm | Not Detectable |
| Myclobutanil | 0.39 ppm | Not Detectable |
| Pyrethrins | 5.36 ppm | Not Detectable |
| Spiromesifen | 11.9 ppm | Not Detectable |
| Trifloxystrobin | 3.38 ppm | Not Detectable |

In addition, it should be understood that although the above-described methods of removing contaminants from plant-derived pharmaceuticals, plant-derived pharmaceuticals and methods of using plant-derived pharmaceuticals are described as "comprising" one or more components or steps, the above-described methods of removing contaminants from plant-derived pharmaceuticals, plant-derived pharmaceuticals and methods of using plant-derived pharmaceuticals may "comprise," "consists of," or "consist essentially of" the above-described method steps and components of the methods of removing contaminants from plant-derived pharmaceuticals, plant-derived pharmaceuticals and methods of using plant-derived pharmaceuticals. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a method of removing contaminants from plant-derived pharmaceuticals, plant-derived pharmaceutical, and/or method of using plant-derived pharmaceuticals that "comprises" a list of elements (e.g., components or steps) is not necessarily limited to only those elements (or components or steps), but may include other elements (or components or steps) not expressly listed or inherent to the method of removing contaminants from plant-derived pharmaceuticals, plant-derived pharmaceutical, and/or method of using plant-derived pharmaceuticals.

As used herein, the transitional phrases "consists of" and "consisting of" exclude any element, step, or component not specified. For example, "consists of" or "consisting of" used in a claim would limit the claim to the components, materials or method steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a method of removing contaminants from plant-derived pharmaceuticals, plant-derived pharmaceutical, and/or method of using plant-derived pharmaceuticals that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described methods of removing contaminants from plant-derived pharmaceuticals, plant-derived pharmaceuticals, and/or methods of using plant-derived pharmaceuticals may comprise, consist essentially of, or consist of any of the herein-described components, method steps, and/or features, as shown in the figures with or without any feature(s) not shown in the figures. In other words, in some embodiments, the methods of removing contaminants from plant-derived pharmaceuticals, plant-derived pharmaceuticals, and/or methods of using plant-derived pharmaceuticals of the present invention do not have any additional features other than those shown in the figures, and such additional features, not shown in the figures, are specifically excluded from the methods of removing contaminants from plant-derived pharmaceuticals, plant-derived pharmaceuticals, and/or methods of using plant-derived pharmaceuticals. In other embodiments, the methods of removing contaminants from plant-derived pharmaceuticals, plant-derived pharmaceuticals, and/or methods of using plant-derived pharmaceuticals of the present invention do have one or more additional features that are not shown in the figures.

The present invention is described above and further illustrated below by way of claims, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

What is claimed is:

1. A method of removing contaminants from a *Cannabis* plant-derived pharmaceutical, said method comprising:
reacting one or more contaminants within a *Cannabis* plant-derived extract with an alkali metal hydroxide in a polar solvent to form one or more contaminant by-products in a reaction mixture, wherein said reacting step comprises:
adding the *Cannabis* plant-derived extract to the alkali metal hydroxide in the polar solvent to form the reaction mixture;
agitating the reaction mixture with mixing; and
adding a neutralizing acid to the reaction mixture, wherein the neutralizing acid comprises glacial acetic acid, or a dilute mineral acid comprising hydrochloric acid, sulfuric acid, or nitric acid; and
separating the one or more contaminant by-products from the *Cannabis* plant-derived extract so as to obtain a contaminant-reduced *Cannabis* plant-derived extract, wherein said separating step comprises:
adding a first alkane to the reaction mixture so as to form a non-aqueous liquid phase within the reaction mixture, wherein the first alkane comprises butane, pentane, cyclopentane, hexane, cyclohexane, heptane, octane, isooctane, or any combination thereof; and
separating an upper non-aqueous liquid phase from a lower aqueous liquid phase, the upper non-aqueous liquid phase comprising the first alkane and the contaminant-reduced *Cannabis* plant-derived extract,
wherein the contaminant-reduced *Cannabis* plant-derived extract comprises one or more cannabinoids.

2. The method of claim 1, wherein the one or more contaminants comprise one or more pesticides, one or more herbicides, one or more fungicides, or any combination thereof.

3. The method of claim 1, wherein the one or more contaminants comprise one or more hydrolyzable pesticides.

4. The method of claim 1, wherein the alkali metal hydroxide comprises lithium hydroxide, sodium hydroxide, potassium hydroxide, or calcium hydroxide.

5. The method of claim 1, wherein the polar solvent comprises methanol; the neutralizing acid comprises hydrochloric acid; and the first alkane comprises hexane, heptane, or any combination thereof.

6. The method of claim 1, further comprising:
passing the upper non-aqueous liquid phase through one or more columns with each column comprising one or more adsorbents; and
collecting an effluent exiting the one or more columns.

7. The method of claim 6, wherein the one or more adsorbents comprise magnesium silicate, activated alumina, magnesium salt of activated alumina, sodium sulfate, silica, bonded phase silica, polymeric non-ionic reversed phase resins, or any combination thereof.

8. The method of claim 7, wherein the one or more adsorbents comprise (i) silica gel in a first column, and (ii) magnesium silicate in a second column.

9. The method of claim 6, further comprising:
passing one or more column volumes of a rinse mixture through the one or more columns, the rinse mixture comprising heptane and ethyl acetate at a heptane:ethyl acetate ratio of about 80:20 by volume; and
collecting the rinse mixture exiting the one or more columns.

10. The method of claim 9, further comprising:
evaporating the rinse mixture under reduced pressure so as to (1) remove one or more of: (i) the first alkane, (ii) heptane, (iii) ethyl acetate, and (iv) any residual neutralizing acid, and (2) result in the contaminant-reduced *Cannabis* plant-derived extract.

11. A method of removing contaminants from a plant-derived pharmaceutical, said method comprising:
reacting one or more contaminants within a plant-derived extract with an alkali metal hydroxide in a polar solvent to form one or more contaminant by-products in a reaction mixture; and
separating the one or more contaminant by-products from the reaction mixture so as to obtain a contaminant-reduced plant-derived extract,
wherein said reacting step comprises:
adding the plant-derived extract to the alkali metal hydroxide in the polar solvent to form the reaction mixture;
agitating the reaction mixture with mixing; and
adding a neutralizing acid to the reaction mixture, wherein the neutralizing acid comprises hydrochloric acid; and
wherein said separating step comprises:
adding a first alkane to the reaction mixture so as to form a non-aqueous liquid phase within the reaction mixture;
separating an aqueous liquid phase of the reaction mixture from the non-aqueous liquid phase;
passing the non-aqueous liquid phase through one or more columns with each column comprising one or more adsorbents;
passing one or more column volumes of a rinse mixture through the one or more columns, the rinse mixture comprising a second alkane and ethyl acetate; and
evaporating the rinse mixture under reduced pressure so as to (1) remove one or more of: (i) the first alkane, (ii) the second alkane, (iii) ethyl acetate, and (iv) any residual neutralizing acid, and (2) result in the contaminant-reduced plant-derived extract.

12. The method of claim 11, wherein (a) the second alkane comprises heptane, and (b) the rinse mixture comprises (i) the heptane, and (ii) up to about 20 weight percent (wt %) of the ethyl acetate.

13. The method of claim 11, wherein the one or more contaminants comprise one or more pesticides, one or more herbicides, one or more fungicides, or any combination thereof.

14. The method of claim 11, wherein the one or more contaminants comprise one or more hydrolyzable pesticides.

15. The method of claim 11, wherein the contaminant-reduced plant-derived extract comprises one or more cannabinoids.

16. The method of claim 14, wherein the contaminant-reduced plant-derived extract comprises one or more cannabinoids.

17. A method of removing contaminants from a plant-derived pharmaceutical, said method comprising:
reacting one or more contaminants within a plant-derived extract with an alkali metal hydroxide in a polar solvent to form one or more contaminant by-products in a reaction mixture, the one or more contaminants comprising one or more pesticides, one or more herbicides, one or more fungicides, or any combination thereof; and
separating (i) the one or more contaminant by-products, and (ii) a contaminant-reduced plant-derived extract from the reaction mixture,
wherein said separating step comprises:
adding a first alkane to the reaction mixture so as to form a non-aqueous liquid phase within the reaction mixture;
separating an aqueous liquid phase of the reaction mixture from the non-aqueous liquid phase;
passing the non-aqueous liquid phase through one or more columns with each column comprising one or more adsorbents;
passing one or more column volumes of a rinse mixture through the one or more columns, the rinse mixture comprising a second alkane and ethyl acetate; and
evaporating the rinse mixture under reduced pressure so as to (1) remove one or more of: (i) the first alkane, (ii) the second alkane, (iii) ethyl acetate, and (2) result in the contaminant-reduced plant-derived extract.

18. The method of claim 17, wherein said reacting step comprises:
adding the plant-derived extract to the alkali metal hydroxide in the polar solvent to form the reaction mixture;
agitating the reaction mixture with mixing; and
adding a neutralizing acid to the reaction mixture, wherein the neutralizing acid comprises hydrochloric acid.

19. The method of claim 18, wherein the one or more contaminants comprise one or more hydrolyzable pesticides.

20. The method of claim 17, wherein the contaminant-reduced plant-derived extract comprises one or more cannabinoids.

* * * * *